(12) United States Patent
Choi (10) Patent No.: US 6,544,218 B1
(45) Date of Patent: Apr. 8, 2003

(54) CATHETER WITH BIASED SHAFT

(75) Inventor: Steven B. Choi, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 125 days.

(21) Appl. No.: 09/625,823

(22) Filed: Jul. 26, 2000

(51) Int. Cl.[7] .............................................. A61M 29/00
(52) U.S. Cl. ................................... 604/96.01; 606/194
(58) Field of Search .......................... 604/96.01, 103.14, 604/93.01, 46, 19, 95.04; 606/194, 195, 108; 623/1.11

(56) References Cited

U.S. PATENT DOCUMENTS

| 5,222,966 A | * | 6/1993 | Perkins et al. ............... 606/194 |
| 5,368,566 A | | 11/1994 | Crocker ....................... 604/101 |
| 5,496,275 A | | 3/1996 | Sirhan et al. .................. 604/96 |
| 5,509,900 A | * | 4/1996 | Kirkman ....................... 604/104 |
| 5,569,184 A | | 10/1996 | Crocker et al. ................ 604/53 |
| 5,662,712 A | * | 9/1997 | Pathak et al. ................ 606/195 |
| 5,743,875 A | | 4/1998 | Sirhan et al. .................. 604/96 |
| 5,797,878 A | * | 8/1998 | Bleam .......................... 606/194 |
| 5,807,355 A | * | 9/1998 | Ramzipoor et al. ......... 604/282 |
| 5,868,706 A | * | 2/1999 | Cox .......................... 604/96.01 |
| 5,879,324 A | | 3/1999 | von Hoffmann .............. 604/49 |
| 5,938,582 A | * | 8/1999 | Ciamacco, Jr. et al. ......... 600/3 |
| 6,036,697 A | * | 3/2000 | DiCaprio ...................... 606/108 |
| 6,165,195 A | * | 12/2000 | Wilson et al. ............... 606/194 |
| 6,235,042 B1 | * | 5/2001 | Katzman ..................... 606/159 |
| 6,428,567 B2 | * | 8/2002 | Wilson et al. ............. 623/1.11 |
| 2001/0047149 A1 | * | 11/2001 | Traxler et al. ........... 604/96.01 |
| 2002/0072755 A1 | * | 6/2002 | Bigus et al. ................. 606/108 |

* cited by examiner

Primary Examiner—Thomas Denion
Assistant Examiner—Thai-Ba Trieu
(74) Attorney, Agent, or Firm—Fulwider Patton Lee & Utecht, LLP (57) ABSTRACT

A catheter including an elongated shaft having a proximal end, a distal end, at least one lumen, and at least a section with a major transverse dimension and a minor transverse dimension, such that the shaft preferentially bends in the direction of the minor transverse dimension. In one embodiment, the catheter is a balloon catheter having a balloon on a distal shaft section, and having a prosthesis mounted on the balloon. In a presently preferred embodiment the prosthesis has a first end and a truncated second end, and is mounted on the balloon such that the truncated second end tapers in the direction of the minor transverse dimension of the shaft. In another embodiment, the catheter has an operative member, such as a drug delivery balloon or an atherectomy member or a radiation, sonic, or light emitter, disposed on or within a distal shaft section, the operative member having an operative surface facing in a direction substantially aligned with the minor transverse dimension of the shaft. The shaft preferentially bends in the direction of the minor transverse dimension, to thereby provide improved ability to position a prosthesis or the operative surface of a catheter operative member in a desired orientation within a patient's body lumen.

20 Claims, 4 Drawing Sheets

CATHETER WITH BIASED SHAFT

BACKGROUND OF THE INVENTION

This invention relates to the field of medical devices, and more particularly to a catheter having a shaft with a minor transverse dimension and a major transverse dimension.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter, and the expanded stent is left in place within the artery at the site of the dilated lesion.

One difficulty has been the use of stents at bifurcation lesions, also known as ostial lesions, in which a lesion is located in a branch vessel at the intersection of the branch vessel and the main vessel. Complicated stenting techniques are used which require multiple balloon catheters and multiple wires, and which frequently result in sub-optimal or improper stent placement due to the difficulty of precise positioning of the stent in the branched anatomy.

It would be significant advance to provide a catheter with improved ability to position the operative distal end of the catheter.

SUMMARY OF THE INVENTION

The invention is directed to a catheter including an elongated shaft having a proximal end, a distal end, at least one lumen, and at least a section with a major transverse dimension and a minor transverse dimension, such that the shaft preferentially bends in the direction of the minor transverse dimension. In one embodiment, the catheter is a balloon catheter having a balloon on a distal shaft section, and having a prosthesis mounted on the balloon. In a presently preferred embodiment, the prosthesis has a first end and a truncated second end, and is mounted on the balloon such that the truncated second end tapers in the direction of the minor transverse dimension of the shaft. In another embodiment, the catheter has an operative member, such as a drug delivery balloon, an atherectomy member, or an emitter such as a radiation, sonic, or light emitter, disposed on or within a distal shaft section, and the operative member has an operative surface facing in a direction aligned with the direction of the minor transverse dimension of the shaft. The shaft preferentially bends in the direction of the minor transverse dimension, to thereby provide improved ability to position a prosthesis or the operative surface of a catheter operative member in a desired orientation within a patient's body lumen.

In the embodiment of the invention in which a prosthesis having a truncated end is mounted on the balloon, a variety of different prostheses may be used including stents, grafts, and the like. In a presently preferred embodiment of the invention, a balloon catheter, which in accordance with the invention has a shaft having a minor transverse dimension and a major transverse dimension, has an angulated ostial stent mounted on the balloon. The angulated ostial stent has a truncated end which is configured to align with an ostium of a branch lumen of a bifurcated body lumen. With the stent mounted on the balloon so that the truncated end tapers in the direction of the shaft minor transverse dimension, the balloon catheter will bend to thereby position the truncated end of the stent in the correct orientation or 180° out of phase within the branch body lumen. By limiting the different possible orientations in which the stent arrives at the bifurcated lesion site, the catheter provides improved ability to correctly position the stent. By visualizing the stent, as for example by fluoroscopy of a radiopaque stent, the physician can determine if the stent is correctly positioned or is 180° out of correct position in the branched body lumen. If the stent is 180° out of phase with the ostium of the branched body lumen, the catheter can be torqued from outside the patient to turn the catheter balloon 180°, to thereby correctly orient the angulated ostial stent. In addition to correctly positioning angulated ostial stents in a patient's body lumen, the catheter of the invention can be used to correctly position a variety of rotational orientation-sensitive devices such as aperture stenting devices, drug delivery devices, radiation, sonic or light delivery devices, where lesion or location specific placement is desired. For example, in one embodiment, a radiation source wire within a lumen of the catheter shaft has a radiation emitting surface facing in a direction aligned with the minor transverse dimension of the shaft, so that the radiation emitting surface faces towards the major transverse dimension of the shaft.

The terminology major transverse dimension and minor transverse dimension should be understood to mean that at least a section of the shaft extending all or part of the length of the shaft has a width in a first direction (i.e., the minor transverse dimension) which is less than a width in a second direction (i.e., the major transverse dimension), the second direction typically being perpendicular to the first direction. Thus, the aspect ratio between the minor transverse dimension and the major transverse dimension is less than one. The preferred aspect ratio between the minor transverse dimension and the major transverse dimension depends on a variety of factors including the catheter application, the nature of the material used to form the shaft, the catheter and catheter lumen dimensions, and the catheter lumen function. In one embodiment, the aspect ratio of the minor to the major transverse dimension is preferably about 1:1.5 (0.67) to about 1:4 (0.25).

The catheter shaft of the invention having a major transverse dimension and a minor transverse dimension may have a variety of suitable shapes including oblong, triangular, and dumbbell shaped transverse cross sections. Additionally, a variety of suitable catheter configurations may be used including a dual lumen shaft, and a dual member shaft having an inner and outer tubular member. In a presently preferred embodiment, the catheter is caused to passively assume the preferential bent shape when the catheter is advanced within the turns of a patient's vasculature. However, in alternative embodiments, the catheter may be provided with a deflection mechanism such as a deflection wire which can be activated, as for example by pulling the wire, to deflect the distal end of the catheter.

The catheter of the invention provides improved positioning of angulated ostial stents and other rotational orientation specific members, due to the orientation of the stent or other member on the catheter relative to the major transverse dimension and the minor transverse dimension of the catheter shaft. These and other advantages of the invention will become more apparent from the following detailed description of the invention and the accompanying exemplary drawings.

DETAILED DESCRIPTION OF THE INVENTION

Figures 1, 2, 3:
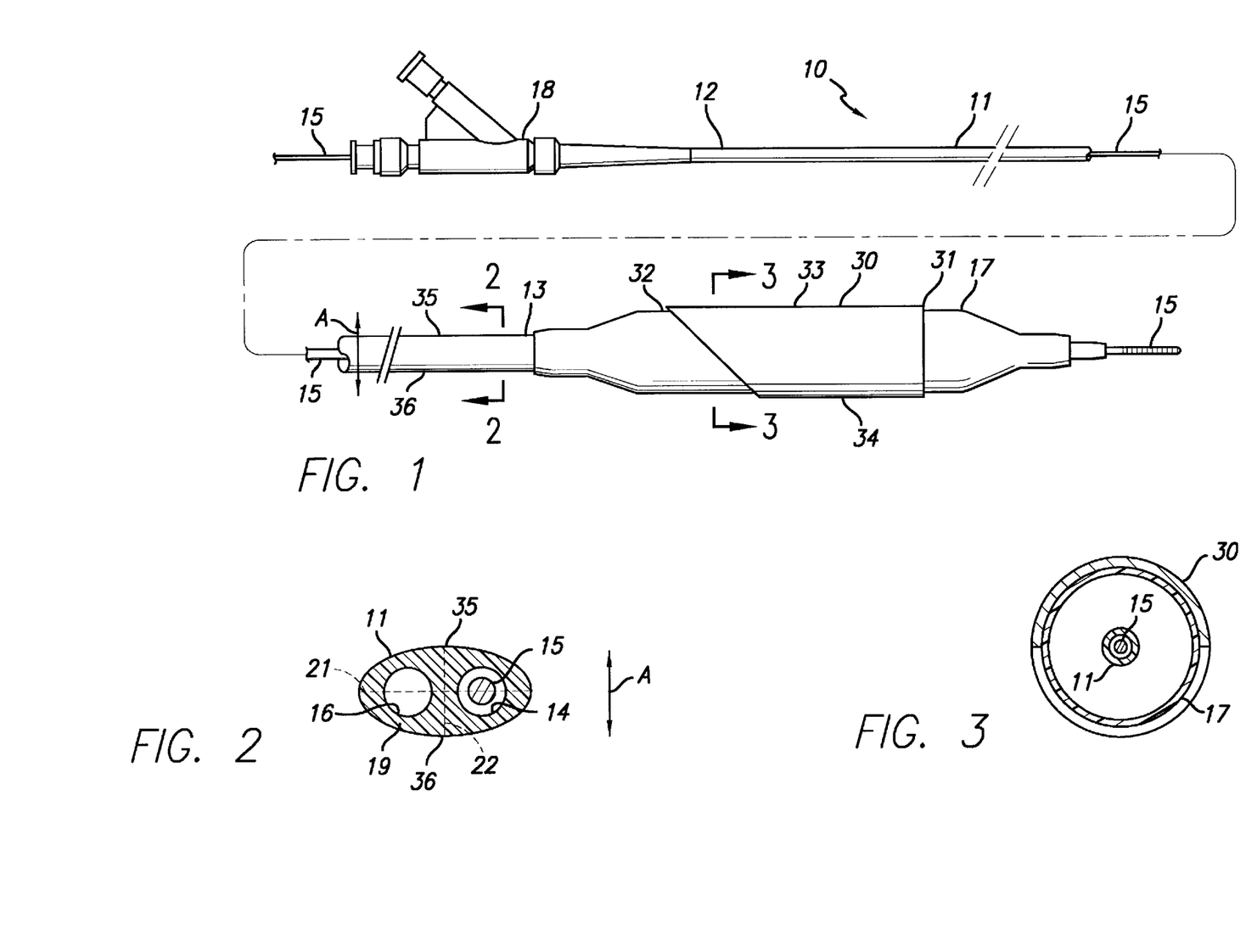
FIG. 1 is an elevational view, partially in section, of a balloon catheter which embodies features of the invention, having an angulated ostial stent on the balloon.
FIG. 2 is a transverse cross sectional view of the balloon catheter shown in FIG. 1, taken along line 2—2.
FIG. 3 is a transverse cross sectional view of the balloon catheter shown in FIG. 1, taken along line 3—3.

FIG. 1 illustrates a balloon catheter 10 which embodies features of the invention. Catheter 10 generally comprises an elongated catheter shaft 11 having a proximal end 12, a distal end 13, a guidewire lumen 14 (FIG. 2) adapted to slidingly receive a guidewire 15, and an inflation lumen 16 (FIG. 2). In the embodiment illustrated in FIG. 1, the shaft 11 is a dual lumen shaft, typically extruded or otherwise formed as a single member with the guidewire lumen 14 and inflation lumen 16 in a side-by-side relationship, so that the guidewire lumen 14 and inflation lumen 16 are each inside and defined by the wall 19 of the dual lumen shaft 11. The distal end of the inflation lumen 16 is proximal to the distal end of the guidewire lumen 14, so that a section of the shaft defining a distal section of the guidewire lumen defines the distal end of the shaft 11. An inflatable balloon 17 is disposed on a distal section of catheter shaft 11, having a proximal end and a distal end sealingly secured to the shaft 11, so that its interior is in fluid communication with inflation lumen 16. An adapter 18 at the proximal end of catheter shaft 11 is configured to direct inflation fluid into inflation lumen 16 and provide access to guidewire lumen 15. A stent 30 is mounted on the balloon 17.

Figure 4:
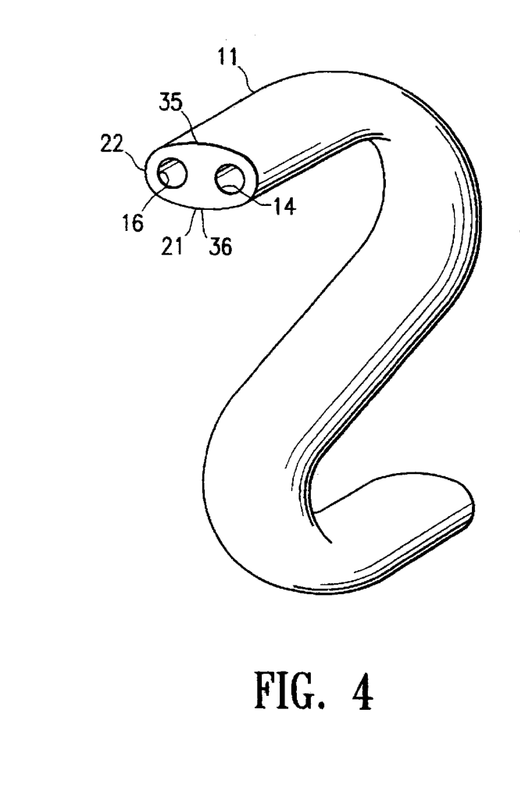
FIG. 4 is a perspective view of the balloon catheter shown in FIG. 1, illustrating the shaft bending in the direction of the minor transverse dimension.

As best shown in FIG. 2, illustrating a transverse cross section of shaft 11 shown in FIG. 1 taken along lines 2-2, shaft 11 has a major transverse dimension 21 and a minor transverse dimension 22. In the illustrated embodiment, the shaft 11 has an oblong transverse cross section, and the minor transverse dimension is in a direction perpendicular to the major transverse dimension. The direction of the minor transverse dimension 22 is illustrated by the arrow A in FIGS. 1 and 2. The width of the shaft in the direction of the minor transverse dimension is smaller than the width of the shaft in the direction of the major transverse dimension. As a result, the shaft 11 preferentially bends in the direction of the minor transverse dimension, as best illustrated in FIG. 4, showing a perspective view of the catheter shown in FIG. 1, with the shaft 11 bending in the direction most easily assumed by the shaft, i.e., the shaft most easily bends in the direction of a line parallel to the minor width of the shaft. In the embodiment illustrated in FIG. 1, the minor transverse dimension 22 is visible, and the major transverse dimension 21 is oriented into and out of the page. Thus, the shaft 11 preferentially bends within the plane of the page in the orientation illustrated in FIG. 1. In FIG. 2, the major and minor transverse dimensions are illustrated with broken lines 21/22. In the additional figures, for illustration purposes, the major transverse dimension 21 and the minor transverse dimension 22 are labeled as the sides of the shaft 11 corresponding to the major and minor widths of the shaft 11, respectively.

Figure 5:
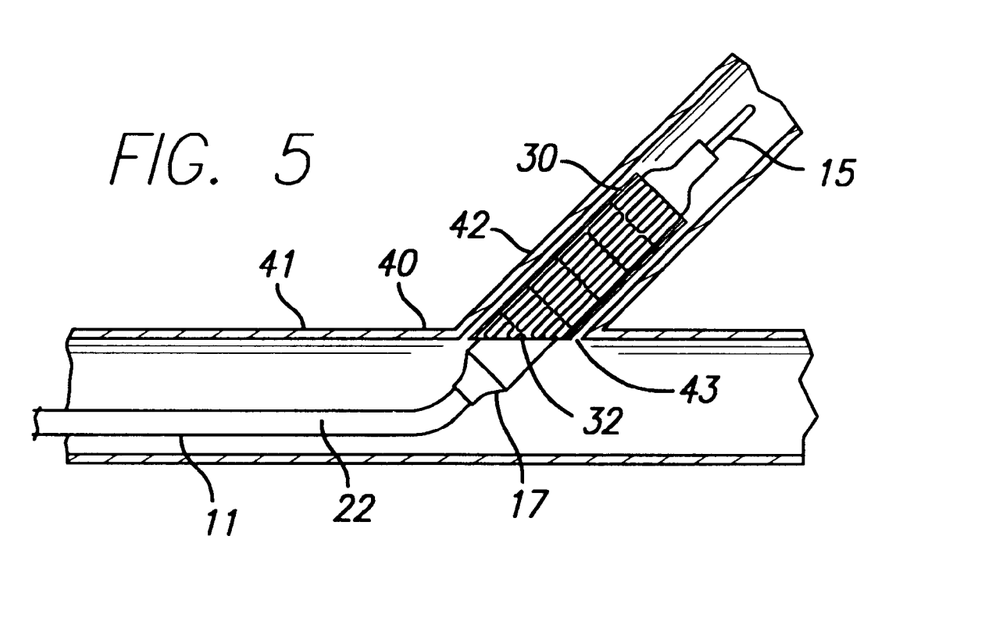
FIG. 5 illustrates the balloon catheter shown in FIG. 1, with the balloon positioned in a branch body lumen of the bifurcated body lumen, and the stent truncated end aligned with the ostium of the branch body lumen.
Figure 6:
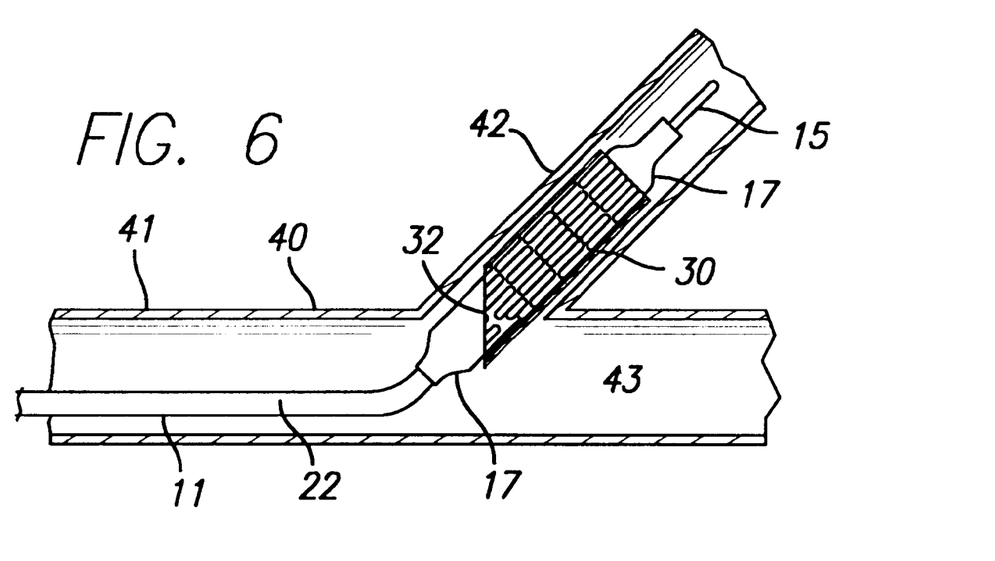
FIG. 6 illustrates the balloon catheter shown in FIG. 1, with the balloon positioned in a branch body lumen of the bifurcated body lumen, with the stent 180° out of phase from the aligned position illustrated in FIG. 5.

Stent 30, mounted on balloon 17, has a first end 31 and a truncated second end 32. The truncated second end 32 tapers in a direction of the minor transverse dimension of the shaft, i.e., the truncated end 32 of the stent has a proximal end aligned with a first side 35 of the minor transverse dimension and a distal end aligned with an opposite side 36 of the minor transverse dimension. As illustrated in FIGS. 1, 5 and 6, the stent has a longer length side 33 and a shorter length side 34 opposite to the longer length side, and the stent 30 is mounted on the balloon 17 so that the longer length side 33 is on the first side 35 of the minor transverse dimension 22 of the shaft and the shorter length side 34 is on the opposite side 36 of the minor transverse dimension 22 of the shaft, so that the truncated second end 32 of the stent 30 tapers in the direction of the minor transverse dimension 22 from the first side 35 to the opposite side 36 of the minor transverse dimension. FIG. 3 illustrates a transverse cross sectional view of the catheter shown in FIG. 1, taken along line 3—3.

In the embodiment illustrated in FIG. 1, the first end 31 of the stent is the distal end of the stent, and the truncated second end 32 of the stent is the proximal end of the stent. However, depending on the approach used to position the balloon 17 in the branch vessel of a bifurcated blood vessel, the truncated end 32 may alternatively be on the distal section of the balloon working length.

FIG. 5 illustrates the balloon catheter 10 shown in FIG. 1, during delivery of the stent 30 to a patient's bifurcated body lumen 40 having a main body lumen 41, such as the aorta or the left anterior descending artery, and a branch body lumen 42 having an ostium 43 at the bifurcation. With the stent 30 mounted on the balloon 17 so that the truncated end 32 of the stent tapers in the direction of the minor transverse dimension 22 of the shaft 11, the catheter 10 is advanced, typically over a guidewire, within the patient's body lumen. For example, the catheter 10 can be advanced over the guidewire from the main body lumen 41 into the branch body lumen 42. The catheter shaft 11 bends during advancement into the branch body lumen 42, and because the shaft bends preferentially in the direction of the minor transverse dimension 22 of the shaft 11, the shaft will naturally orient itself so that the truncated end 32 of the stent 30 is either aligned with the ostium 43 of the branch body lumen 42, or 180° out of alignment with the ostium 43, i.e., 180° out of phase to the aligned position illustrated in FIG. 5. FIG. 5 illustrates the truncated end 32 of the stent 30 aligned with the ostium 43 of the branch body lumen 42. As illustrated in FIG. 5, the angle of the truncated end 32 of the stent 30 is designed to match the angle of the ostium 43 of the branch lumen 42, so that when aligned with the ostium 43, the face of the truncated end 32 of the stent 30 extends along the face of the ostium without being proximal or distal to the ostium 43. As illustrated in FIG. 6, the balloon 17 may be advanced into the branch body lumen 42 with the truncated end 32 of the stent 30 180° out of alignment with the ostium 43. Consequently, the physician viewing the position of the stent under fluoroscopy rotates shaft 11 to turn the distal end of the catheter and the balloon 17 and stent 30 thereon 180°, to thereby position the stent 30 in the desired orientation in the branch body lumen 42 with the truncated end 32 of the stent 30 aligned with the ostium 43. With the stent 30 in the desired orientation in the branch body lumen 42, inflation medium is delivered to the balloon 17 to inflate the balloon 17 and expand the stent 30 thereon. The balloon 17 is deflated and the catheter 10 is withdrawn from the body lumen, leaving the expanded stent 30 implanted therein.

A variety of conventional stent designs for stent 30 may be used in the stent assembly of the invention, including commercially available stents such as the MULTILINK or TRISTAR, available from Guidant, modified to have the angulated ostial stent truncated end discussed herein. The stent 30 is preferably formed of a radiopaque material such as stainless steel, nickel titanium alloy, or tantalum. The angle of the truncated end 32 of the stent 30 will vary depending on the application of the stent 30, and is generally about 20° to about 80°, more specifically about 30° to about 60°.

In the embodiment illustrated in FIG. 1, the shaft 11 has a multilumen configuration having the inflation lumen 16 and the guidewire lumen 14 in a side by side relationship. Alternatively, catheter 10 may have the guidewire lumen disposed inside the inflation lumen, which in one embodiment generally comprises an elongated catheter shaft having an outer tubular member and an inner tubular member disposed within outer tubular member (not shown). Inner tubular member defines a guidewire lumen adapted to slidingly receive a guidewire. The coaxial relationship between outer tubular member and inner tubular member defines annular inflation lumen. In one embodiment, an inflatable balloon is disposed on a distal section of catheter shaft, having a proximal end sealingly secured to the distal end of outer tubular member and a distal end sealingly secured to the distal end of inner tubular member so that its interior is in fluid communication with inflation lumen. In a presently preferred embodiment, the outer tubular member has a major transverse dimension and a minor transverse dimension as discussed above with regard to the embodiment shown in FIG. 1, so that the shaft preferentially bends in the direction of the minor transverse dimension of the outer tubular member. The inner tubular member may similarly have a major transverse dimension and minor transverse dimension, or alternatively, it may have a circular transverse cross section. In an alternative embodiment, the inner tubular member has a minor and major transverse dimension in accordance with the invention, and the outer tubular member has a circular cross section.

Figure 7:
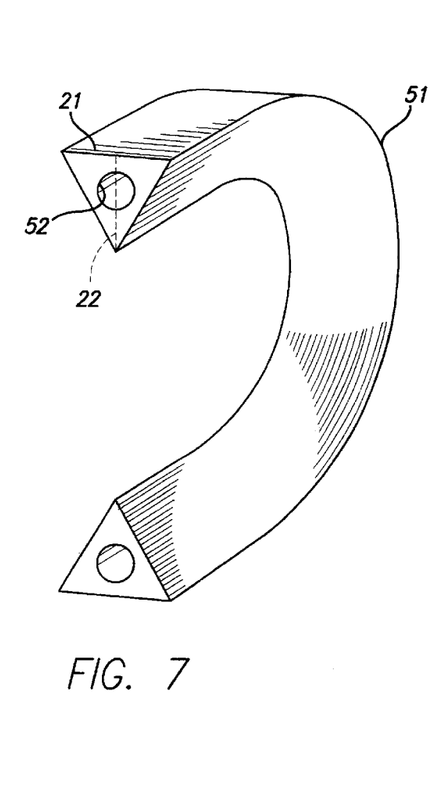
FIG. 7 is a perspective view of a section of an alternative embodiment of a catheter which embodies features of the invention, having a triangular shaped shaft bending in the direction of the minor transverse dimension.
Figure 8:
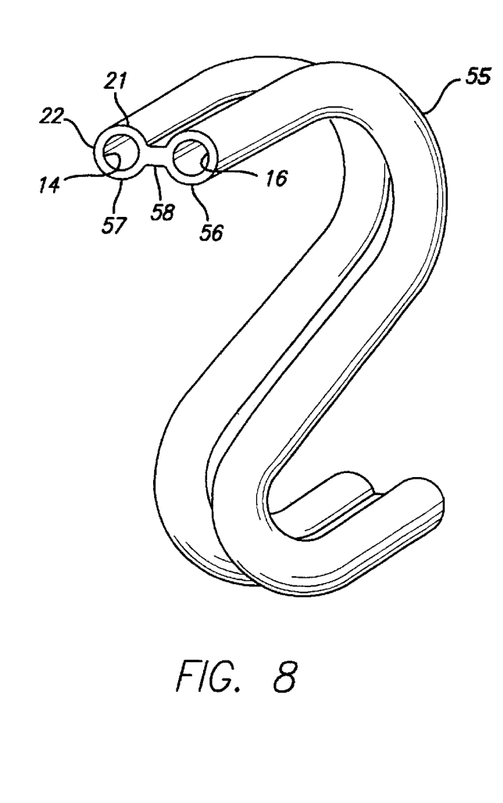
FIG. 8 is a perspective view of a section of an alternative embodiment of a catheter which embodies features of the invention, having a dumbbell shaped shaft bending in the direction of the minor transverse dimension.

The catheter shaft having a major transverse dimension 21 and a minor transverse dimension 22 may have a variety of suitable configurations. In the embodiment illustrated in FIG. 1, shaft 11 has an oblong transverse cross section. FIG. 7 illustrates an alternative embodiment in which shaft 51 has lumen 52, and has a triangular transverse cross section with major transverse dimension 21 and minor transverse dimension 22. Although illustrated as an equilateral triangular cross section, the shaft 51 may alternatively have a variety of triangular shapes such as an isosceles triangular cross section. Additionally, in alternative embodiments, shaft 51 may have two or more lumens. FIG. 8 illustrates an alternative embodiment in which shaft 55 has a dumbbell shaped transverse cross section having a first circular section 56 and a second circular section 57 on opposite ends of bridging section 58 having a smaller outer diameter than the outer diameter of the circular sections 56/57. The first circular section 56 defines inflation lumen 16 and the second circular section 57 defines a second lumen such as guidewire lumen 14. It should be understood that the discussion herein relating to shaft 11 applies to the embodiment of the catheter 10 having triangular shaft 51 or dumbbell shaft 55.

Figures 9, 10, 10A, 11, 12:
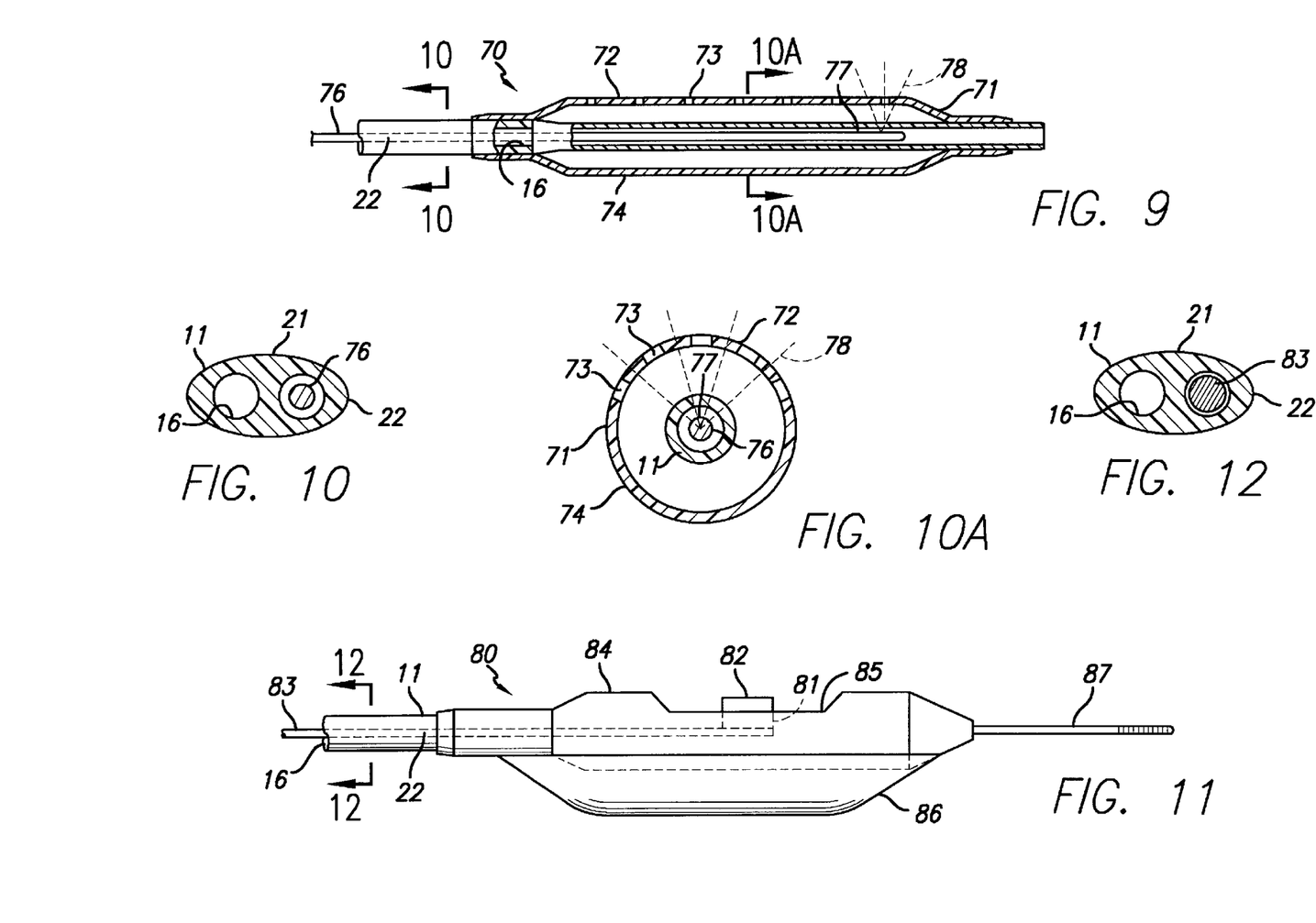
FIG. 9 is an elevational view, partially in section, of the distal end of a radiation and drug delivery catheter which embodies features of the invention, having a radiation emitting wire in catheter lumen and a drug delivery balloon.
FIG. 10 is a transverse cross sectional view of the catheter shown in FIG. 9, taken along line 10—10.
FIG. 10A is a transverse cross sectional view of the catheter shown in FIG. 9, taken along line 10—10.
FIG. 11 is an elevational view, partially in section, of the distal end of an atherectomy catheter which embodies features of the invention.
FIG. 12 is a transverse cross sectional view of the catheter shown in FIG. 11, taken along line 12—12.

FIGS. 9–12 illustrate alternative embodiments of the catheter of the invention generally comprising an elongated shaft 11, which in accordance with the invention has a major transverse dimension 21 and a minor transverse dimension 22, and an operative member having an operative outer surface configured to perform a medical procedure disposed on or within a distal section of the shaft 11 such that at least a section of the operative surface faces in a direction substantially aligned with the direction of the minor transverse dimension 22. The terminology substantially aligned should be understood to mean that the operative surface faces in a direction aligned with the direction of the minor transverse dimension or at least closer to the direction of the minor transverse dimension 22 than to the major transverse dimension. In the embodiment illustrated in FIG. 9, operative member is balloon 71 of catheter 70. Balloon 71 has an operative outer surface comprising a permeable wall 72 configured to deliver a fluid, such as a diagnostic or therapeutic fluid, from within the balloon into a patient's body lumen. In the illustrated embodiment, the permeable wall 72 comprises holes or ports 73 within a working length of the balloon 71. However, a variety of different configurations may be used to form the permeable wall 72, such as are commonly employed in drug delivery balloon designs. It should be understood that, for illustration purposes, the ports 73 are not shown to scale. The shaft 11 bends preferentially in the direction of the minor transverse dimension, as discussed herein in relation to balloon catheter 10, to facilitate positioning of the permeable wall 72 of the balloon 71 in the desired orientation to deliver fluid from within the balloon to a specific site in the patient's body lumen. FIG. 10 illustrates a transverse cross sectional view of the catheter shaft 11 shown in FIG. 9, taken along lines 10—10. In a presently preferred embodiment, the operative outer surface is on a section of the operative member which does not extend around the entire outer surface of the operative member. Thus, the operative member has a outer surface with at least a section which does not perform the function of the operative outer surface. In the embodiment illustrated in FIG. 9, an opposite outer surface 74 of the balloon, opposite from the permeable wall operative surface 72, is solid-walled. The permeable wall operative surface 72 extends from a first point to a second point on the balloon circumference, the first and second points being aligned with opposite sides of the major transverse dimension of the shaft 11. In one embodiment, the permeable wall operative surface 72 is on one half of the balloon circumference, so that the surface 72 extends from a first point to a second point on the balloon circumference, the first and second points being aligned with opposite ends of the opposite sides of the major transverse dimension of the shaft 11. Alternatively, the permeable wall operative surface may extend over a section of the balloon circumference which is less than one half of the balloon circumference, as illustrated in FIG. 10A, illustrating a transverse cross sectional view of the catheter 70 shown in FIG. 9, taken along line 10A—10A.

In an alternative embodiment, the operative member is a energy emitter. FIG. 9 illustrates an emitter 76 with an operative outer surface 77 in the catheter shaft 11, configured to emit radiation 78 within a patient's body lumen. Although illustrated in the fluid delivery balloon 71 having a permeable wall 72, the radiation emitter 76 could be used in a variety of catheters including non-fluid delivery balloon catheters and delivery catheters. The radiation emitting operative outer surface 77 faces in a direction aligned with or substantially aligned with the direction of the minor transverse dimension 22, so that shaft 11 bends preferentially in the direction of the minor transverse dimension 22 to facilitate positioning of the radiation emitting surface 77 in the desired orientation for delivering radiation energy 78 to a specific site in the patient's body lumen. In alternative embodiments, the emitter 76 is configured to emit energy in the form of sonic or light energy.

In an alternative embodiment illustrated in FIG. 11, atherectomy catheter 80 has an operative member comprising a cutting member 81. Cutting member 81 has an operative outer surface 82 configured to cut or otherwise remove structures such as lesions from within a body lumen. The cutting member operative outer surface 82 faces in a direction aligned with or substantially aligned with the direction of the minor transverse dimension 22, so that shaft 11 bends preferentially in the direction of the minor transverse dimension 21 to facilitate positioning of the cutting member 81 in the desired orientation for contacting and removing a lesion in the patient's body lumen. It should be understood that a variety of different, conventional atherectomy catheter designs can be used in the catheter of the invention. In the illustrated embodiment, catheter 80 includes a drive shaft 83 for driving the cutting member 81. Catheter has housing 84 containing the cutting member 81, the housing 84 having a window 85 through which cutting member 81 contacts material within the patient's body lumen to be removed during an atherectomy procedure. A balloon 86 on one side of the catheter shaft 11 is in fluid communication with inflation lumen 16 in shaft 11, and can be inflated to move or push the distal end of the catheter 80 so that the cutting member contacts material to be removed. FIG. 12 illustrates a transverse cross sectional view of the catheter shown in FIG. 11, taken along line 12—12 . It should be understood that the discussion herein relating to the balloon catheter 10 applies to catheters 70/80.

The shaft 11 may be formed of a variety of materials commonly used in the production of catheter shafts, including polyurethanes, polyolefins, polyesters, polyamides and elastomers. Preferably, the shaft polymeric material, or materials where a blends or layers of multiple materials are used, is sufficiently hard to provide a shaft which provides the benefit of preferentially bending in the direction of the minor transverse dimension. Softer materials may be used where the shaft has reinforcements such as metal braids. In a presently preferred embodiment the shaft is formed of polyamide such as amorphous Nylon 12.

In a presently preferred embodiment, the width of the shaft in the direction of the minor transverse dimension is about 25% to about 75% smaller, and most preferably about 30% to about 60% smaller than the width of the shaft in the direction of the major transverse dimension. The width of the shaft 11 in the direction of the minor transverse dimension 22 is about 0.015 inch (0.38 mm) to about 0.125 inch (3.2 mm), more preferably about 0.032 inch (0.81 mm) to about 0.052 inch (2.7 mm), and the width of the shaft in the direction of the major transverse dimension 21 is about 0.039 inch (1 mm) to about 0.175 inch (4.4 mm) more preferably about 0.065 inch (1.65 mm) to about 0.105 inch (2.7 mm).

The dimensions of catheter 10 are determined largely by the size of the guidewires to be employed and the size of the artery or other body lumen through which the catheter must pass or the size of the stent being delivered. Typically, the inflation lumen 16, or the outer tubular member, has an inner diameter of about 0.015 to about 0.035 inch (0.038 to 0.089 cm), usually about 0.03 inch (0.076 cm). The section defining the distal section of guidewire lumen 14 distal to the inflation lumen, or the inner tubular member, typically has an outer diameter of about 0.012 to about 0.020 inch (0.030 to 0.051 cm), usually about 0.017 inch (0.043 cm). The overall working length of the catheter 10 may range from about 80 to about 160 cm, and is typically about 140 cm. Preferably, balloon 17 may have a length about 0.5 cm to about 5 cm and typically about 3 cm with an inflated working diameter of about 1 to about 10 mm.

The balloon catheter 10 may be configured for use in a variety of applications, including use as a dilatation catheter having a dilatation balloon, a stent delivery catheter, a drug delivery catheter, and the like. The balloon catheter illustrated in FIG. 1 is an over-the-wire catheter. In a presently preferred embodiment of the invention, the balloon catheter is an over-the-wire catheter due to the improved torqueability of the over-the-wire design relative to other catheter shaft designs. However, various balloon catheter designs may be used, such as rapid exchange and fixed wire catheters. Rapid exchange catheters typically have an elongated shaft with a proximal end, a distal end with a balloon on a distal shaft section in fluid communication with an inflation lumen, a distal port in the distal end of the catheter, a proximal port spaced a substantial distance from the proximal end of the catheter closer to the distal end than to the proximal end, and a short guidewire lumen extending between the proximal and distal ports.

The invention has been discussed in terms of certain preferred embodiments. One of skill in the art will recognize that various modifications may be made without departing from the scope of the invention. For example, while illustrated primarily in terms of a multilumen shaft, the shaft may comprise an inner and outer tubular member, one or both of which have the major and minor transverse dimension configuration in accordance with the invention. Additionally, in the embodiment having an operative member with an operative outer surface, the operative outer surface may face in a direction aligned or substantially aligned with the major transverse dimension, if desired. Moreover, while certain features may be shown or discussed in relation to a particular embodiment, such individual features may be used on the various other embodiments of the invention.

What is claimed is:

1. A balloon catheter, comprising
   a) an elongated shaft having a proximal end, a distal end, an inflation lumen, and at least a section with a major transverse dimension and a minor transverse dimension, such that the shaft preferentially bends in a direction of the minor transverse dimension;
   b) a balloon on a distal shaft section having an interior in fluid communication with the inflation lumen; and
   c) a prosthesis having a first end, and a truncated second end, the prosthesis being mounted on the balloon such that the truncated second end tapers in the direction of the minor transverse dimension of the shaft.

2. The balloon catheter of claim 1 wherein the shaft has an oblong transverse cross section.

3. The balloon catheter of claim 1 wherein the shaft has a triangular transverse cross section.

4. The balloon catheter of claim 1 wherein the shaft has a dumbbell shaped transverse cross section having a first and a second circular section on opposite ends of a bridging section with a smaller outer diameter than the circular sections.

5. The balloon catheter of claim 4 wherein the first circular section of the shaft defines the inflation lumen, and the second circular section of the shaft defines a second lumen.

6. The balloon catheter of claim 1 wherein the shaft comprises a dual lumen shaft having a wall, wherein the inflation lumen and a second lumen are inside and defined by the wall of the dual lumen shaft.

7. The balloon catheter of claim 1 wherein the shaft comprises an inner tubular member defining a lumen configured to receive a guidewire therein, and an outer tubular member defining the inflation lumen, the outer tubular member having the major transverse dimension and the minor transverse dimension.

8. The balloon catheter of claim 7 wherein the inner tubular member has a circular transverse cross section.

9. The balloon catheter of claim 7 wherein the inner tubular member has the major transverse dimension and the minor transverse dimension.

10. The balloon catheter of claim 1 wherein the width of the shaft in the direction of the minor transverse dimension of the shaft is about 25% to about 75% smaller than the width of the shaft in the direction of the major transverse dimension of the shaft.

11. The balloon catheter of claim 1 wherein the width of the shaft in the direction of the minor transverse dimension of the shaft is about 0.38 mm to about 3.2 mm, and the width of the shaft in the direction of the major transverse dimension is about 1 mm to about 4.4 mm.

12. A catheter, comprising
    a) an elongated shaft having a proximal end, a distal end, at least one lumen, and at least a section with a major transverse dimension and a minor transverse dimension, such that the shaft preferentially bends in a direction of the minor transverse dimension; and
    b) an operative member having an operative outer surface configured to perform a medical procedure, the operative member being disposed on or within a distal section of the shaft such that the operative surface faces in a direction substantially aligned with the direction of the minor transverse dimension of the shaft.

13. The catheter of claim 12 wherein the operative member includes an opposite outer surface which is different from the operative surface and which is radially displaced from the operative surface on an opposite side of the operative member.

14. The catheter of claim 12 wherein the operative member is a balloon having an operative outer surface having an open-walled permeable wall configured to deliver a fluid from within the balloon into a patient's body lumen.

15. The catheter of claim 14 wherein the operative member includes an opposite outer surface which is solid-walled and which is radially displaced from the open-walled operative surface on an opposite side of the operative member.

16. The catheter of claim 12 wherein the operative member is an atherectomy member having an operative outer surface comprising a cutting member.

17. The catheter of claim 12 wherein the operative member is a an emitter selected from the group consisting of radiation emitter, sonic emitter and light emitter, with an operative outer surface configured to emit energy within a patient's body lumen.

18. A method of performing a medical procedure, comprising
    a) positioning within a body lumen a balloon catheter, comprising
       i) an elongated shaft having a proximal end, a distal end, an inflation lumen, and at least a section with a major transverse dimension and a minor transverse dimension, such that the shaft preferentially bends in a direction of the minor transverse dimension;
       ii) a balloon on a distal shaft section having an interior in fluid communication with the inflation lumen; and
       iii) a prosthesis having a first end, and a truncated second end, the prosthesis being mounted on the balloon such that the truncated second end tapers in the direction of the minor transverse dimension of the shaft;
    b) advancing the catheter within the patient's body lumen to a branch lumen of a lumen bifurcation, and positioning the balloon within the branch lumen, so that the catheter is bent in the direction of the minor transverse dimension of the shaft; and
    c) inflating the balloon to implant the prosthesis in the branch lumen with the truncated end of the prosthesis aligned with an ostium of the branch lumen at the bifurcation.

19. The method of claim 18 including before (c), rotating the catheter about 180° to align the truncated end of the prosthesis with the ostium.

20. A method of performing a medical procedure, comprising
- a) positioning within a body lumen a catheter, comprising
  - i) an elongated shaft having a proximal end, a distal end, at least one lumen, and at least a section with a major transverse dimension and a minor transverse dimension, such that the shaft preferentially bends in a direction of the minor transverse dimension; and
  - ii) an operative member having an operative outer surface configured to perform a medical procedure, the operative member being disposed on or within a distal section of the shaft such that the operative surface faces in a direction substantially aligned with the direction of the minor transverse dimension of the shaft; and
- b) advancing the catheter within the patient's body lumen to position the operative member at a desired location within the body lumen, with the catheter bent in the direction of the minor transverse dimension of the shaft; and
- c) activating the operative member to perform the medical procedure within the body lumen with the operative surface of the operative member facing in the direction in which the catheter is bent and aligned in the direction of the minor transverse dimension of the shaft.

\* \* \* \* \*